United States Patent [19]

Talley

[11] Patent Number: 4,533,769

[45] Date of Patent: Aug. 6, 1985

[54] METHOD OF MAKING METHYLATED PHENOL FROM METHYLATED CYCLOHEXENEONE

[75] Inventor: John J. Talley, Clifton Park, N.Y.

[73] Assignee: General Electric Company, Schenectady, N.Y.

[21] Appl. No.: 613,545

[22] Filed: May 24, 1984

[51] Int. Cl.$^3$ ................... C07C 37/07; C07C 37/00
[52] U.S. Cl. ................................. 568/806; 568/763
[58] Field of Search .................. 568/806, 805, 763

[56] References Cited

U.S. PATENT DOCUMENTS

| 2,369,196 | 2/1945 | Williams et al. | 568/806 |
|---|---|---|---|
| 2,369,197 | 2/1945 | Winkler et al. | 568/806 |
| 3,803,249 | 4/1974 | Rieve | 568/806 |
| 3,816,546 | 6/1974 | Rieve | 568/806 |
| 4,086,282 | 4/1978 | Wattimena | 568/806 |
| 4,453,025 | 1/1984 | Van Seters et al. | 568/806 |

FOREIGN PATENT DOCUMENTS

| 0080759 | 6/1983 | European Pat. Off. | 568/806 |
|---|---|---|---|
| 1197802 | 7/1980 | United Kingdom | 568/806 |

Primary Examiner—Werren B. Lone
Attorney, Agent, or Firm—William A. Teoli; James Magee, Jr.; James C. Davis, Jr.

[57] ABSTRACT

A method is provided for making 3,5-dimethylphenol from isophorone by catalytic demethanation using as a catalyst, the calcination residue of a mixture of magnesium carbonate and/or magnesium hydroxide and a manganese compound.

3 Claims, No Drawings

METHOD OF MAKING METHYLATED PHENOL FROM METHYLATED CYCLOHEXENEONE

BACKGROUND OF THE INVENTION

Prior to the present invention various methods were available for making methylated phenols such as 3,5-xylenol from isophorone. Methylated phenols such as 3,5-dimethylphenol are important as intermediates for the preparation of antibacterials such as 4-chloro-3,5-dimethylphenol.

For example, B. V. Maatschappij, German Offen. No. 2,529,773 shows the conversion of isophorone to 3,5-dimethylphenol in the gas phase using a Co-MoK catalyst on aluminum oxide, where the catalyst was calcined at 900°–1200° C. There is shown in U.S. Pat. No. 3,803,249 a method of making 3,5-xylenol by acetone condensation. A mixture of acetone, water and tetralin are contacted with a magnesium oxide catalyst at a temperature of 371° C.–510° C. Winkler et al, U.S. Pat. No. 2,369,197 shows the conversion of isophorone to 3,5-xylenol by gas phase pyrolysis over activated alumina at 450°–500° C. Additional procedures for converting isophorone to 3,5-xylenol are shown by F. Wattimena, U.S. Pat. No. 3,641,166 and H. G. Frank, K. Ruhl and J. Turowski, U.S. Pat. No. 4,086,282 involving the employment of methyl iodide to convert isophorone to 3,5-xylenol.

The present invention is based on the discovery that 3,5-dimethylphenol can be made by pyrolysis of isophorone. Catalytic demethanation of isophorone can be achieved with an effective amount of the calcination residue of a mixture of magnesium carbonate and/or magnesium hydroxide and a manganese compound as defined hereinafter.

STATEMENT OF THE INVENTION

There is provided by the present invention, a method for making a methylated phenol having the formula,

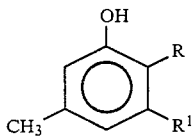

which comprises (1) pyrolyzing a polymethylated cyclohexene-1-one having the formula

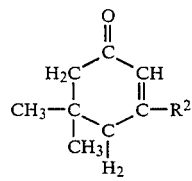

in the presence of an effective amount of a demethanation catalyst consisting essentially of the calcination residue of a mixture of magnesium carbonate and/or magnesium hydroxide and a manganese compound (2) recovering the methylated phenol from the mixture of (1), where R is a member selected from hydrogen or methyl, $R^1$ is a member selected from hydroxy, $-OR^3$ and methyl, $R^2$ is selected from methyl and $-OR^3$ and $R^3$ is a $C_{(1-6)}$ alkyl radical.

Some of the methylated phenols of formula 1 which can be made in accordance with the practice of the present invention, are for example, 3,5-dimethylphenol, 5-methylrecorcinol, and meta-cresol.

There are included by the polymethylated cyclohexeneones which are employed in the practice of the present invention as shown by formula (2) compounds such as isophorone, 3-methyl-5,5-dimethylcyclohexen-1-one, and 5,5-dimethylcyclohexen-1-one.

The catalyst of the present invention in the form of a calcination residue of a mixture of magnesium carbonate and/or magnesium hydroxide and a manganese compound can be made by combining magnesium carbonate and/or magnesium hydroxide and manganese hydroxide with subsequent calcination at elevated temperatures to form the active catalyst composite. Manganese hydroxide can be precipitated in the presence of basic magnesium carbonate, that is $XMgCo_3 \cdot Mg(OH)_2 \cdot XH_2O$, where X can be from about 3 to about 5. The manganese hydroxide can be generated from a water soluble salt of manganese, for example, manganese nitrate, which forms a precipitate of manganese hydroxide in the presence of the basic magnesium carbonate. The resulting mixture of basic magnesium carbonate and manganese hydroxide, which can be present at from 1 to 10% by weight of the uncalcined mixture, can be shaped into convenient catalyst pellets in paste form by extrusion, molding or other conventional shaping techniques. Calcination of the pellets can be effected at temperatures of from 300°–500° C. or higher during the demethanation of the methylated cyclohexeneone. If desired, water soluble synthetic resins, such as polyphenylene oxide, polyvinylalcohol polymers, acrylics, sodium carboxymethylcellulose and the like, can be used as shaping aids in the wet pelleting of the magnesium-manganese catalyst composite. A preferred polyphenylene oxide is poly-(2,6-dimethyl-1,4-phenylene)oxide, hereinafter referred to as polyphenylene oxide.

In the practice of the invention, the polymethylated cyclohexeneone of formula (2) is pyrolyzed at a temperature in the range of from 300° C. to 700° C. in the presence of an effective amount of the calcination residue of a mixture of magnesium carbonate and/or magnesium hydroxide and a manganese compound, referred to hereinafter as "demethanation catalyst". An effective amount of the demethanation catalyst means that there can be utilized from about 5% to 50% based on the weight of polymethylated cyclohexenone prior to being pyrolyzed. Preferably, the demethanation catalyst is utilized in pelletized form and part of a pelletized blend with a thermoplastic such as polyphenylene oxide. In making the pelletized blend of the demethanation catalyst, there can be used from 40 to 80 parts of the calcination residue of the mixture of magnesium carbonate and/or magnesium hydroxide and manganese compound as previously defined per 100 parts of the polyphenylene oxide which is defined in Hay, U.S. Pat. No. 3,308,875. Calcination of the magnesium carbonate and/or magnesium hydroxide and a manganese compound mixture is preferably effected prior to the pyrolysis of the polymethylated cyclohexene-1-one, referred to hereinafter as the "methylated cyclohexenone". Pyrolysis of the methylated cyclohexenone can be effected at a temperature in the range of from 350° C. to 675° C. while passing over the demethanation catalyst at liquid hourly space velocity (LHSV) of from 0.1 to 10.0 and preferably of from 0.5 to 3.0. In calculating LHSV, the volume of the feed, for example, the methylated cyclohexanone per hour can be divided by the volume of the demethanation catalyst utilized in the pyrolysis reaction. Calculation of the volume of the demethanation of the volume of the demethanation catalyst can be made while the demethanation ctalyst is in the uncalcined state.

It has been found that the pyrolysis of the methylated cyclohexenone can be expressed on a weight basis as follows:

$$WHSV = \frac{\text{weight of the feed passed over the catalyst in an hour}}{\text{weight of the uncalcined demethanation catalyst}}$$

In converting LHSV to WHSV, a density of about 0.8 for the uncalcined magnesium carbonate mixture can be used. In addition, the demethanation catalys can experience a weight loss of about 30 to 70% based on the weight of the original uncalcined mixture.

Recovery of the desired methylated phenol from the reaction effluent can be achieved by conventional procedures such as distillation, crystallization, etc. For example, the reaction effluent can be dissolved in an aliphatic organic solvent such as hexane. The methylated phenol such as 3,5-xylenol will crystallize out at ambient temperature or upon cooling to 0° C.

In order that those skilled in the art will be better able to practice the invention, the following examples are given by way of illustration and not by way of limitation. All parts are by weight unless otherwise indicated.

EXAMPLE 1

A slurry of 518.9 grams of "basic" MgCo3 in 2000 ml of distilled water was combined with 40.0 grams of Mn(NO3)2, diluted to 500 ml with distilled water over approximately a 4-minute time period. 10.8 grams of a 50% caustic NaOH solution diluted to 500 ml with distilled water was added to the resulting admixture over approximately 4 minutes, followed by stirring for one hour at room temperature. The slurry was vacuum filtered, washed with 1500 ml of distilled water, resuspended by homogenizing in water and vacuum filtered again. The "resuspension" procedure was repeated four times for a total of five resuspensions and five vacuum filtrations. The filtrate was dried overnight under vacuum in a 103° C. oven and ground to a fine powder. The powder was blended with sufficient polyphenylene oxide to provide 90 parts by weight of "basic" MgCO3 co-precipitated with Mn(OH)2 and 10 parts by weight of polyphenylene oxide. The 90:10 powder blend was precompressed in a tableting press, ground and sifted through a #25 screen, and tableted to form 3/16"×⅛" pellets.

There was placed into an electrically heated vertical quartz 2 (30 cm×25 mm), 5 cm of quartz chips, 20 cm of the above magnesium carbonate blend with polyphenylene oxide and 5 cm of quartz chips. The components in the reactor were then heated at a temperature in the range of about 400° C. for 2-4 hours to calcinate the magnesium carbonate blend. Pure isophorone was then passed over the resulting demethanation catalyst in a stream of dry nitrogen at various flow rates. The resulting products were then analyzed by gas liquid chromatography. The following results were obtained, following the above procedure at a temperature of 500° C. and an LHSV of 0.5

TABLE I

| Weight % | Component |
| --- | --- |
| 91.4 | 3,5-Xylenol |
| 3.6 | 2,3,5-Trimethylphenol |

The above mixture is dissolved in hexane. The resulting solution is cooled to about 0° C. and 3,5-xylenol is allowed to crystallize out. The identity of the product is confirmed by its melting point of 66° C. and is recovered at substantially the same yield as shown in Table I.

EXAMPLE 2

The procedure of Example 1 was repeated, except that in place of isophorone there was utilized 5,5-dimethyl-3-ethoxy-2-cyclohexene-1-one. There was obtained a mixture of 5-methylresorcinol and 3-ethoxy-5-methylphenol having a proportion of 10 parts of the resorcinol to 1 part of the phenol.

EXAMPLE 3

The procedure of Example 1 was repeated, except that a temperature of 400° C. was maintained during the pyrolysis. The following results were obtained:

TABLE II

| Weight % | Component |
| --- | --- |
| 40.6 | Isophorone |
| 54.6 | 3,5-Xylenol |
| 1.6 | 2,3,5-Trimethylphenol |

EXAMPLE 4

The procedure of Example 1 was repeated, except that the LHSV was 2.5. There was obtained a mixture of 30.4% of isophorone, 61% of 3,5-xylenol and 1.6% of 2,3,5-trimethylphenol. The identity of the products were confirmed by comparison with authentic samples and GC, NMR, IR and the melting point.

EXAMPLE 5

The procedure of Example 1 was repeated, except that the pyrolysis was conducted utilizing an LHSV of 5. It was found that the resulting product was a mixture of 15% of 3,5-xylenol and 80% of unreacted isophorone. Following the same procedure at an LHSV of 1, there was obtained a mixture of 93.4% by weight of 3,5-xylenol and 4.2% by weight of 2,3,5-trimethylphenol.

Although the above examples are directed to only a few of the very many variables which can be used in the practice of the present invention, it should be understood that the present invention is directed to a much broader variety of demethanation catalysts and polymethylated cyclohexanones as shown by formula 2, resulting in the production of a much broader variety of methylated phenols.

What I claim as new and desired to secure by Letters Patent of the United States is:

1. A method for making a methylated phenol having the formula,

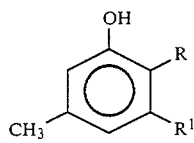

which comprises (1) pyrolyzing at a temperature in the range of from

300° C. to 700° C., a polymethylated cyclohexene- 1-one having the formula

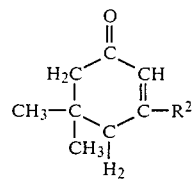

in the presence of an effective amount of a demethanation catalyst consisting essentially of the calcination residue of a mixture of magnesium carbonate and/or magnesium hydroxide and a manganese compound (2) recovering the methylated phenol from the mixture of (1), where R is a member selected from hydrogen or methyl, $R^1$ is a member selected from hydroxy, $-OR^3$ and methyl, $R^2$ is selected from methyl and $-OR^3$ and $R^3$ is a $C_{(1-6)}$ alkyl radical.

2. A method in accordance with claim 1, where the methylated cyclohexanone is isophorone.

3. A method in accordance with claim 1, where the methylated phenol is 3,5-dimethylphenol.

* * * * *